United States Patent [19]
Collins et al.

[11] Patent Number: 5,408,865
[45] Date of Patent: Apr. 25, 1995

[54] TRANSDERMAL CELL TEST MATTER VOLUME-ADJUSTMENT DEVICE

[76] Inventors: Charles C. Collins, 220 Ashland Ave., Pittsburgh, Pa. 15228-2212; Amy C. Little, 2385 Hanover West La., Atlanta, Ga. 30327; Pradeepkumar P. Sanghvi, 219 Coltart Ave., First Floor, Pittsburgh, Pa. 15213-3101; Henry Hofer, 30 Brace Dr., E. Hanover, N.J. 07936; James E. Swon, 12 Twin Pk. Dr., Brookside, N.J. 07926

[21] Appl. No.: 106,555

[22] Filed: Aug. 16, 1993

Related U.S. Application Data

[63] Continuation-in-part of Ser. No. 882,241, May 8, 1992, abandoned, which is a continuation-in-part of Ser. No. 651,286, Feb. 4, 1991, abandoned, which is a continuation-in-part of Ser. No. 617,560, Nov. 26, 1990, Pat. No. 5,108,710.

[51] Int. Cl.[6] .................. A61F 13/56; G01N 13/00
[52] U.S. Cl. ........................... 73/38; 73/64.47; 422/101; 424/449
[58] Field of Search ............ 73/864.83, 863.23, 64.55, 73/49.2; 422/101, 102, 449

[56] References Cited

U.S. PATENT DOCUMENTS

| | | | |
|---|---|---|---|
| 3,590,634 | 7/1971 | Pasternak | 73/159 |
| 4,137,756 | 2/1979 | Cosack et al. | 73/63.3 |
| 4,667,504 | 5/1987 | Hobson | 73/38 |
| 4,695,551 | 9/1987 | Samhaber et al. | 73/863.23 |
| 4,771,004 | 9/1988 | Higuchi | 436/5 |
| 5,108,710 | 4/1992 | Little et al. | 422/104 |
| 5,139,951 | 8/1992 | Butz et al. | 435/284 |
| 5,306,420 | 4/1994 | Bisconte | 210/143 |

Primary Examiner—Hezron E. Williams
Assistant Examiner—J. David Wiggins
Attorney, Agent, or Firm—William T. Hough

[57] ABSTRACT

In a transdermal cell, a matter volume-adjustment male device includes the lower opening end of the through-space structure having inner wall female threads mateable with first male threads of a screwable matter volume-adjustment male member alternately adjustable upwardly and downwardly between opposite upper and lower female threads-termination points. The screwable matter volume-adjustment member has opposite first upper and lower male threads-termination points, and the inner wall female threads are further concurrently mateable with a bottom closure member having second male threads having opposite second upper and lower male threads-termination points. There is a first annular sealing ring sealably mounted in an annular groove around the screwable volume-adjustment male member between the first upper and lower threads-termination points positioned between the inner wall female threads and the first male threads, and there being a second annular sealing ring sealably mounted the second male threads at a location below the second upper termination point.

10 Claims, 2 Drawing Sheets

TRANSDERMAL CELL TEST MATTER VOLUME-ADJUSTMENT DEVICE

This application is a continuation-in-part of application U.S. Ser. No. 07/882,241 filed May 8, 1992, abandoned Apr. 16, 1994 as a continuation-in-part of U.S. Ser. No. 07/651,286, abandoned May 8, 1992, filed Feb. 4, 1991 as a continuation-in-part of U.S. Ser. No. 07/617,560 filed Nov. 26, 1990/U.S. Pat. No. 5,108,710 as of Apr. 28, 1992. The above-stated application disclosures are incorporated by reference into this disclosure.

PRIOR ART

Based on a prior art search of Class 73, subclass 64.3, no relevant patents were found. Including United patent previously made of record in foregoing patent applications, other areas of search include Class 604, subclasses 304 and 307, and class 73, subclasses 73, 76 and 866, and class 428, subclass 254. Patents of interest include U.S. Pat. 4,137,756 to Cosack et al. and U.S. Pat. No. 3,590,634 to Pasternak and U.S. Pat. No. 4,771,004 to Higuchl. None of the foregoing patents are directed to nor suggestive of nor designed for a transdermal cell to be utilizable within a dissolution vessel, nor for the potential nor suggested achieving of the express objects of the present invention. Bach of the foregoing patents are directed to pumping separate segregated liquids into contact with opposite sides of a membrane and there is no foreseeable way nor manner in which such patent-disclosed structures could be utilized for comparable testing of already fully-fabricated transdermal patches. Subsequent testing of transdermal patches incorporating previously tested membranes, would be under vastly different and non-comparable conditions and test procedures - thereby defeating the express objects of the present invention. None of the foregoing patents even remotely relate to nor suggest the Structure and combination of the present invention.

BACKGROUND TO THE INVENTION

Rigid and inflexible and strongly enforced government standards exist in the control of the pharmaceutical and/or health industry in the testing equipment and accuracy and consistency thereof and reliability thereof, (1) for permeability of transdermal membrane(s) of unknown permeability to one or more liquid(s) of known permeability capability(ies) and/or (2) for the permeability of one or more liquid(s) of unknown permeability capability(ies), to a transdermal membrane of known permeability capability(ies), and/or (3) for the testing of a non-liquid matter of known absorption rate to either a transdermal membrane of unknown permeability with a liquid of known permeability, or for the testing of a non-liquid matter of unknown absorption rate to a transdermal membrane of known permeability using a liquid of known permeability. Factors that are critical to the obtaining of consistent test results typically include the exact volume of liquid in the testing vessel surrounding the transdermal cell, its volume being always a "constant", i.e. the volume of liquid being the same from one test to the next, as a known unchanging constant. Another such factor that can alter the repeatability of test results, is the presence of different pressure of a solute and/or non-liquid matter within a constant-volume reservoir, from one test to another, arising from use of different quantities of the non-liquid matter in different otherwise repetitive tests; such non-constant condition results and arises from availability of different amounts of the same or different non-liquid matter to be tested in otherwise repetitive tests when consecutive identical tests use the same or identical transdermal membranes. The same problem results if the volume of the reservoir for holding the non-liquid matter, varies from one test to another for otherwise identical quantities (volumes) of the non-liquid matter (s) being tested and/or retested for verification. Accordingly, great care heretofore has been essential to assure consistent and reliable repetitive results in testing the same non-liquid matter, or in tests using different non-liquid matter for comparative purposes. Unfortunately, such government requirements are difficult to meet repeatedly with the required degree of accuracy. As set-forth in the following objects, the present invention is directed principally to overcoming such typical prior difficulties in achieving consistent and repeatable results for liquid(s) and/or transdermal membrane(s) and/or non-liquid matter(s) - as the case may be, being tested.

OBJECTS OF THE INVENTION

Objects of the invention include the overcoming of one or more problems and/or difficulties of nature discussed above.

More particularly, an object of the present invention is to provide structure as an integral part of a transdermal cell, to make possible use of different quantities of non-liquid matter in different otherwise repetitive tests, within the reservoir space separated by a transdermal membrane from liquid of known volume within the vessel in which the transdermal cell is immersed, to obtain consistent and reliable repeatable test results as confirmations. Another object is to provide structure as an integral part of a transdermal cell, to make possible use of the same quantities of non-liquid matter in test-holding space of consistently constant pressure with variable space as variable reservoir space separated by a transdermal membrane from liquid of known volume in which the transdermal cell is immersed, to obtain consistent and reliable repeatable test results.

Another object is to provide an easy and/or simple structure embodying mechanism for altering predictably volume of reservoir space and/or repeatedly obtaining constant pressure of reservoir space-contained non-liquid matter against transdermal membrane separating the non-liquid matter from the liquid in which the transdermal cell is immersed, to obtain consistent and reliable repeatable test results.

Other objects become apparent from the preceding and following disclosure.

BROAD STATEMENT OF THE INVENTION

The invention broadly in its most generic description may be described as an improvement in a transdermal cell as follows.

The improvement is a combination of a prior existing transdermal cell, in combination with the improvement. The prior transdermal cell consists essentially of a membrane enhancer tester structure and mechanism thereof for ascertaining transdermal membrane permeability of a transdermal membrane to at least one of a liquid media and a non-liquid matter isolated by said transdermal membrane from the liquid media when the trandsermal membrane is mounted within the liquid media contained within a dissolution vessel having therein a downwardly-directed revolvable linearly-extending stirring shaft that includes a distal end carrying at least one stirring blade within the liquid media. The membrane enhancer tester structure and mechanism are additionally for measuring physical attributes of at least one of the downwardly directed revolvable linearly-extending stirring shaft and the at least one stirring blade 1) when the linearly-extending stirring shaft having the distal end is stably mounted with the stirring blade within the liquid media and 2) the linearly-extending stirring shaft is revolved at a known rate, and when the liquid media is of a predetermined volume sufficiently finite to enable consistently repeatably ascertaining of said transdermal membrane permeability during the revolving of the linearly-extending shaft at said known rate.

The broadly stated improvement consists essentially of:

1) a through space-forming structure:
  a) having an upper opening and having an opposite lower opening interconnected by a container space therebetween having a first diameter of a first dimension, the through space-forming structure at the upper opening including upper seat structure seatable and sealable of the transdermal membrane sufficiently to isolate the container space from the liquid media located above the transdermal membrane; and
  b) including female-threaded structure in juxtaposition to and extending a distance of at-least partially along the container space, the female threaded structure having an upper threads end and a lower threads end:
    [1] the female threaded structure having opposite female threaded structure upper and lower ends thereof; and 2) a volume-adjustment male member:
  a) having male threads mateable with and screwable along the female threaded structure; and
  b) having a maximum second diameter of a second dimension ranging up to the first dimension; and
  c) having a male member upper end and an opposite male member lower end; and 3) a first annular liquid-sealing member:
  a) positioned between the upper threads end and the lower threads end, within the container space; and
  b) being of a size of a predetermined third dimension sufficiently large to prevent passage of the liquid media between the female threaded structure and the male threads when the volume-adjustment male member is screwed to a location partially above and partially below the first annular member; and 4) a bottom closure structure and mechanism thereof for sealing closeably the container space at substantially the opposite lower end when the volume-adjusment member is in a screwed-upwardly location above the female structure lower end, the bottom closure structure having an upper face spaced below the aforestated opposite male member lower end when the volume-adjustment male member is mounted within the container space and when concurrently the bottom closure structure is sealably mounted on lower end of the through space-forming structure.

In a first preferred embodiment as an improvement on the aforestated broad generic invention, the bottom closure structure and mechanism thereof consists essentially of:

a) a bottom closure structure mountable at the opposite lower opening on the through space-forming structure; and
  b) a second annular liquid-sealing member positioned sealably between and in contact with each of the space-forming structure and the volume-adjustment male member at a position located below the opposite male member lower end in a sealing relationship preventative of the liquid media to pass between the opposite male member lower end and space exterior to the container space.

In a second preferred embodiment as an improvement on the first preferred embodiment, the volume-adjustment male member:
  a) has a longitudinal axis; and
  b) includes groove forming a first annular groove around the longitudinal axis at a location between the upper threads end and the lower threads end; and
  c) the first annular liquid-sealing member is mounted sealably within the first annular groove.

In a third preferred embodiment, the bottom closure structure as an improvement on the second preferred embodiment:
  a) includes an upwardly extending bottom closure male member having bottom closure male threads meshable with the female-threaded structure, the bottom closure threads having:
    [1] an upper bottom closure threads end; and
    [2] an opposite bottom closure threads end; and
  b) a closure structure top end in juxtaposition to the upper bottom closure threads; and
  c) further including a closure structure bottom end in juxtaposition to the opposite bottom closure threads end.

In a third preferred embodiment as an improvement on the fourth preferred embodiment, there is included the second annular liquid-sealing member mounted around the upwardly extending bottom closure male member.

In a fifth preferred embodiment as an improvement on the fourth preferred embodiment, there is included as an improvement on the fourth preferred embodiment; the bottom closure structure:
  a) has a transverse axis transverse to the longitudinal axis; and
  b) includes laterally-extending structure extending along the transverse axis in juxtaposition to closure structure bottom end a distance greater than the first dimension as measured from a center of the upwardly extending bottom closure male member.

In a sixth preferred embodiment as an improvement on the fifth preferred embodiment, the volume-adjustment male member includes at the opposite male member lower end a key-receiving structure and mechanism thereof structured for insertion of a key by which the volume-adjustment male member is alternately screwable upwardly and downwardly along the female threaded structure.

In a seventh preferred embodiment, there is included the sixth improvement as an improvement on the aforestated broad generic invention.

In an eighth preferred embodiment, there is included the improvement of the second preferred embodiment as an improvement on the aforestated broad generic invention.

In a ninth preferred embodiment, there is included the improvement of the third preferred embodiment as an improvement to the aforestated broad generic invention.

In a tenth preferred embodiment, as an improvement on the fifth preferred embodiment, the volume-adjustment male member includes at the opposite male member lower end a key-receiving structure and mechanism thereof for insertion of a key by which the volume-adjustment male member is alternately screwable upwardly and downwardly along the female threaded structure.

The invention may be better understood by reference to the following Figures.

THE FIGURES

FIG. 1 is a diagrammatic illustration symbolic of an embodiment embodying each and all preferred embodiments, shown in exploded view with various side cut-away views exhibiting partial cross-section of inner and outer structures and relative relationships thereof.

FIG. 2 is a diagrammatic illustration of the same embodiment as that of FIG. 1, shown in a non-exploded view, also with various cut-away views exhibiting partial cross-section of inner and outer structures and relative relationships thereof, but additionally shown relationship to the phantom illustration of the liquid containing vessel with motor driven shaft and mixing blade thereof in which setting the present invention is utilized.

DETAILED DESCRIPTION

Figure 1:
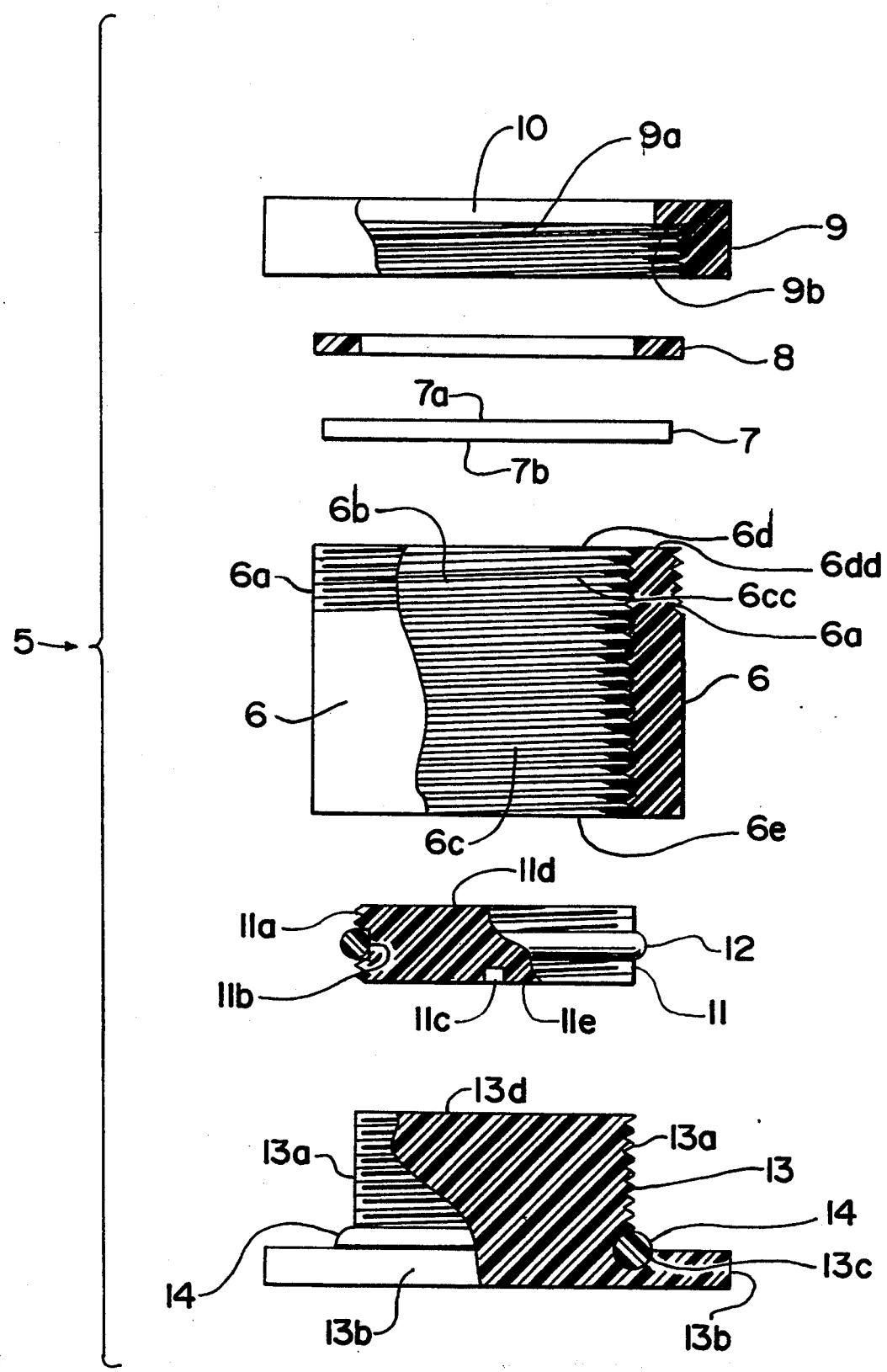

To understand the significance of the present invention, it is important to recognize facts of the foregoing background to the invention, and additionally as follows.

The slightest difference in the exact and always same initial volume of liquid (water or otherwise) 18 contained in the tube-like vessel such as vessel 17 in which the transdermal cell is positioned in a submersed state of being below the revolving stirring blade 19 revolved by the revolving shaft 16 revolved at a predetermined rate of revolutions by the motor 15, can totally invalidate any and all test measurements directed toward precisely ascertaining the government regulated physical data previously discussed. For example, if the volume of a sample of non-liquid matter varies from one test sample to another encased within a retainer reservoir space between a transdermal membrane and encompassing walls circumscribing a container space of constant volume, incorrect and/or inconclusive measurements in transdermal liquid flow rate through the membrane and/or of leaching rate of the enclosed non-liquid matter from the reservoir space will result because of different and/or varying surface area of exposure of the non-liquid matter being pressed against and/or in communication with the transdermal membrane, as well as volume of remaining space-volume within the retainer reservoir space varying and resulting in a greater-volume of water required to leach into that space through the transdermal membrane prior to contact with the non-liquid matter; also, when the non-liquid matter is of insufficient volume to assure it being pressed into contact with the retainer reservoir space-face of the transdermal membrane with always predictable pressure, there result inconclusive and varying measurement as to rate of flow of the liquid through the transdermal membrane and/or rate of leaching of the particular non-liquid matter-sample within the reservoir space. Likewise, the same inconclusive data results when the flow rate of a transdermal membrane and/or the leaching rate is/are known for other liquids and the test is to determine the rate of passage through the same transdermal membrane and/or the rate of leaching of a known non-liquid matter-sample, in attempted ascertainment of data for a different liquid For the particular type of transdermal testing cell to which the present invention is directed, which cell includes a bottom closure member for insertion of a non-liquid sample into a retainer reservoir space for a cell on which the transdermal membrane has already been mounted, this type of transdermal testing cell has the advantage of not having to disturb the previously mounted and sealed transdermal membrane - such operation of mounting the transdermal membrane being much more difficult in structures in which the sample must be added through a top opening prior to sealably mounting the transdermal membrane.

Heretofore the bottom closure ,member has included an upwardly-extending male-insertion structure such that the top end thereof when fully inserted constitutes a bottom face defining the bottom limit of the retainer reservoir space utilizable for containing the non-liquid matter-sample, such space heretofore being always the same because of full maximum insertion of an upwardly-extending male structure of a single bottom closure member prior to the present improvement invention. It is noted that if the bottom closure member were solely partially upwardly inserted, the result would include more thereof extending into the liquid, resulting in a false volume-reading level within the tube-like test vessel, and also would result in absence of a seal at the lower end of the bottom opening by the heretofore utilized bottom edge-located O-sealing ring.

Accordingly, it has been determined as a part of the present invention, that the outside surface area of a transdermal cell must be always constant and the volume (space-displacement) likewise must be always constant, from one test to the next, such that variations in degree of insertion of the bottom male member would not distort the otherwise reliable liquid volume and accurate and meaningful readings for data of the type(s) above-discussed.

Consistent with this/these foregoing inventive recognitions of controlling factors and requirements, the present invention has retained the bottom closure member 13, but has arrived at a critically separate alternately upwardly and downwardly adjustable volume-adjustment male member 11 by which volume of the cell retainer reservoir space 6cc may be altered to accomodate non-liquid samples of different total volumes, but with always a constant pressure of its upper face 11d against the sample whereby the pressure of the sample against the transdermal membrane also is always a constant pressure. This is ascertainable in-part by observing the transdermal membrane from above, during the upward-screwing of the volume-adjustment male member 11 after previously inverting the cell during the mounting of the non-liquid matter sample within the cell retainer reservoir space 6cc. Once the volume-adjustment male member 11 is properly screwably inserted sufficiently to result in a repeatable predetermined constant pressure of the non-liquid matter against a lower face of the transdermal membrane 7, thereafter the bottom closure member is inserted.

It is particularly noted that there critically exists a liquid annular seal 12 associated with the volume-adjustment male member 11 properly sealably mounted therearound against the insertion space walls, in order to prevent any liquid from seeping and/or flowing and/or leaking into space below the volume-adjustment male member, above the bottom closure member; such seepage and/or leakage and/or flow would result in altering ascertainable variations in otherwise constant volume of the liquid within a test vessel exterior to the transdermal cell and/or volume of liquid passing through the transdermal membrane into the cell retainer reservoir space 6cc.

In light of the foregoing explanations by the inventors, the structure of the invention as disclosed in foregoing figures may be more adequately understood, as follows.

Figure 2:
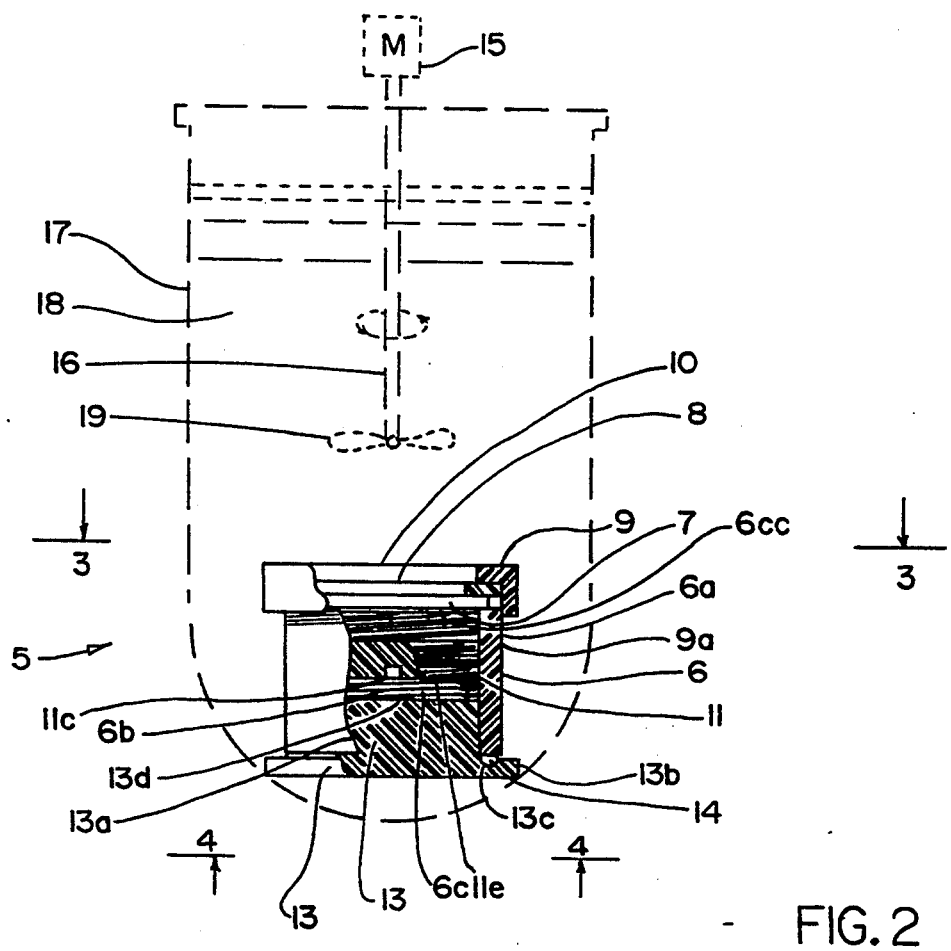
Figure 3:
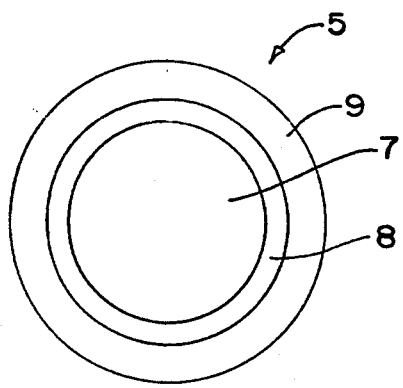
FIG. 3 is a diagrammatic illustration as taken along line 3—3 of FIG. 2.

FIGS. 1 and 2 illustrate substantially the same view of the same overall composite structure and its integral parts, FIG. 1 differing solely in being and exploded view illustration and FIG. 2 being in an integrated combined state. FIG. 3 is an elevation plan view of the top, as aforestated taken along lines 3—3 of FIG. 2, and FIG. 4 is an elevation plan view of the bottom, as aforestated taken along lines 4—4 of FIG. 2.

Figure 4:
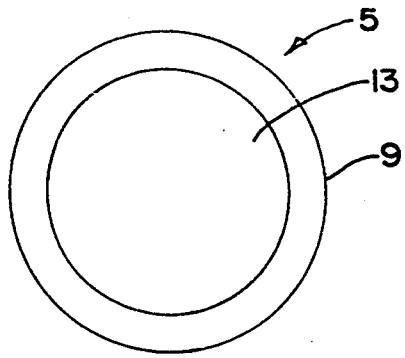
FIG. 4 is a diagrammatic illustration as taken along line 4—4 of FIG. 2.

FIGS. 1, 2, 3 and 4 thus illustrate the claimed transdermal cell 5, with FIGS. 3 and 4 being limited to features viewable from upper and lower view thereof. There is an annular through space-forming, structure 6 (commonly called a cell body) having an upper end and opening thereof 6d and a lower end and opening thereof 6e. The upper and lower openings at respectively upper and lower ends 6d and 6e are interconnected by a through space 6c formed by inside surface of the aforestated annular through-space-forming structure 6. This through space-forming surface is identified as female-threaded structure identified as the female threads 6b. The segment 6cc of the through-space c is the portion immediately below the upper end 6d and constitutes the cell retainer reservoir space 6cc above the upper end (and face) 11d of the volume-adjustment male member 11. In conventional manner, a typically conventional transdermal membrane 7 is mounted on seat-structure 6dd across the upper opening 6d formed by the seat-structure 6dd, in a state of being pressed sealably downwardly onto and against the through space-forming structure 6 by virtue of typically a conventional annular sealing washer 8 (or other equivalent sealing member) held in a downwardly-compressed state by a typically conventional retainer cap 9 having a radially inwardly-extending overhang 9b that presses sealably downwardly onto the annular sealing washer 8 when the retainer cap 9 is in the illustrated state of being downwardly screwed by virtue of its inner female threads 9a in a mating relationship with the outer circumscribing male threads 6a of the through space-forming structure 6. With the retainer cap 9 in its screwed-down state, the through-space opening (hole) 6d is in flow communication with the transdermal membrane 7. The inner diameter of the annular through space 6c is that of a first dimension, as to be compared to dimensions given later in terms of relative size.

A novel cylindrically shaped volume-adjustment male member 11 has upper end and face 11d and lower end and face 11e and male threads 11a, with an annular groove or slot 11b intermediate between the upper end 11d and the lower end 11e, having liquid-sealably mounted therein a sealing ring 12 sealing against flow and/or leakage of liquid from above the end 11d to below the end 11e. Along its lower end and face 11e is a squared notch as a key-receiving structure into which an appropriate key or screwdriver may be inserted to twist and thereby revolve the volume-adjustment male member 11 screwably alternately upwardly and downwardly. The outer diameter of the cylindrically shaped Volume-adjustment male member is a second dimension that ranges upward to slightly less than the first dimension, such that the male threads 6a are screwable within the female threads 6b.

Spaced-below the end 11e a distance of a critically present space 6c is a bottom closure member 13 having upwardly extending cylindrically shaped member 13a having circumscribing male threads 13a screwably meshable with female threads 6b, having upper end and face 13d. The outer diameter of the upwardly extending cylindrically shaped member 11a is a third dimension by which the male threads 11aa are screwable within the female threads 6b.

Accordingly, because after having inverted the transdermal cell 5, removed the bottom closure member 13 and the volume-adjustment male member 11, and after thereafter insertion of the non-liquid matter through the through space 6c to the sub-space, i.e. reservoir space 6cc positioned against the lower face 7b of the transdermal membrane 7, the volume-adjustment male member 11 is screwed upwardly to a degree that its upper face 11d presses firmly against the previously inserted non-liquid matter such that the inserted non-liquid matter is caused to press against the lower face 7b minor or low pressure - assuring good contact of the non-liquid matter with the lower face 7b such that during subsequent testing good leaching thereof is achieved as a liquid transgresses through the transdermal membrane to leach or absorb-away the non-liquid matter to thereafter pass the leached non-liquid matter through the transdermal membrane into liquid exterior to the retainer reservoir space 6cc. The annular washer 8 or an O-ring prevents liquid from passing downward into space beneath the volume-adjustment male member, and the O-ring seal 14 prevents, 18 exterior to the transdermal cell 5 from passing upwardly through the male threads 13a and/or the female thread 6a at the bottom end of the transdermal cell 5, such that the amount of liquid exterior to the transdermal cell remains constant, apart from that leaching through the transdermal cell. The results, is improved., and reliably constant opportunity for leaching resulting from controlled liquid amount in the exterior to the transdermal cell and in the contact of leaching liquid with the non-liquid matter within the reservoir space irrespective of possible difference in the total quantity of non-liquid matter as compared with other tests of the same identical non-liquid matter. Thereby, reliable and comparative data are securable for accurate determinations during repetitive testings.

Composition of the transdermal membrane 7 may be of any heretofore conventional and/or other equivalent and/or substitute transdermal membranes. Heretofore, such membranes have typically been animal skin such as mouse-skin, and typically synthetic ( known as artificial ) transdermal membranes of cellulose or other conventional and/or equivalent or desired compositions found to be effective for use as transdermal membranes. Likewise, for the annular washer 8 heretofore has been found to be preferably a TEFLON (Tm) washer in so far as being an effective seal when pressed downwardly against the outer circumscribing top-surface edges of the transdermal membrane as previously described herein, but it is within the scope of and not the substance of this invention to utilize other equivalent conventional or otherwise desirable annular washers or O-rings, provided such prove to be effective.

It is within the scope of this invention to make variations, modifications and/or substitution of equivalents within the skill of an ordinary artisan in this field.

I claim:

1. A transdermal cell in combination consisting essentially of: in a membrane enhancer tester means for ascertaining transdermal membrane permeability of a transdermal membrane to at least one of a liquid media and a non-liquid matter isolated by said transdermal membrane from the liquid media when the transdermal membrane is mounted within the liquid media contained within a dissolution vessel having therein a downwardly-directed revolvable linearly-extending stirring shaft that includes a distal end carrying at least one stirring blade within the liquid media, and for measuring physical attributes of at least one of the downwardly directed revolvable linearly-extending stirring shaft and the at least one stirring blade when the linearly-extending stirring shaft having the distal end is stably mounted with the stirring blade within the liquid media and when the linearly-extending stirring shaft is revolved at a known rate, and when the liquid media is of a predetermined volume sufficiently finite to enable consistently repeatably ascertaining said transdermal membrane permeability during the revolving of the linearly-extending shaft at said known rate; the improvement consisting essentially of a through space-forming structure having an upper opening at an upper end and having an opposite lower opening at a lower end interconnected by a container space therebetween having a first diameter of a first dimension, the through space-forming structure at said upper opening including upper seat structure seatable and sealable of the transdermal membrane sufficiently to isolate said container space from said liquid media located above the transdermal membrane, and the through space-forming structure including female-threaded structure in juxtaposition to and extending a distance of at-least partially along said container space, said female threaded structure having an upper threads end and a lower threads end, the female threaded structure having opposite female threaded structure upper and lower ends thereof; and a volume-adjustment male member having male threads mateable with and screwable along said female threaded structure and having a maximum second diameter of a second dimension ranging up to said first dimension, the volume-adjustment male member having a male member upper end and an opposite male member lower end; and a first annular liquid-sealing member positioned between said upper threads end and said lower threads end, within said container space and being of a size of a predetermined third dimension sufficiently large to prevent passage of said liquid media between said female threaded structure and said male threads when said volume-adjustment male member is screwed to a location partially above and partially below said first annular liquid-sealing member; and a bottom closure means for sealing closeably said container space at substantially said opposite lower end when said volume-adjustment member is in a screwed-upwardly location above said female structure lower end, the bottom closure structure having an upper face and the upper face being spaced below said opposite male member lower end when the volume-adjustment male member is mounted within the container space and concurrently the bottom closure structure is sealably mounted on the lower end of the through space-forming structure.

2. The transdermal cell of claim 1, in which said bottom closure means consists essentially of a bottom closure structure mountable at said opposite lower opening on said through space-forming structure and a second annular liquid-sealing member positioned sealably between and in contact with each of said through space-forming structure and said volume-adjustment male member at a position located below said opposite male member lower end in a sealing relationship preventative of said liquid media to pass between said opposite male member lower end and space exterior to said container space.

3. The transdermal cell of claim 2, in which said volume-adjustment male member has a longitudinal axis and includes groove forming a first annular groove around said longitudinal axis at a location between said upper threads end and said lower threads end, said first annular liquid-sealing member being mounted sealably within said first annular groove.

4. The transdermal cell of claim 3, in which said bottom closure structure includes an upwardly extending bottom closure male member having bottom closure male threads meshable with said female-threaded structure, said bottom closure threads having an upper bottom closure threads end and an opposite bottom closure threads end and said bottom closure structure including a closure structure top end in juxtaposition to upper bottom closure threads and said bottom closure structure further including a closure structure bottom end in juxtaposition to said opposite bottom closure threads end.

5. The transdermal cell of claim 4, including said second annular liquid-sealing member mounted around said upwardly extending bottom closure male member.

6. The transdermal cell of claim 5, in which said bottom closure structure having a transverse axis transverse to said longitudinal axis and includes laterally-extending structure extending along said transverse axis in juxtaposition to said closure structure bottom end a distance greater than said first dimension as measured from a center of said upwardly extending bottom closure male member.

7. The transdermal cell of claim 6, in which said volume-adjustment male member includes at said opposite male member lower end a key-receiving means for insertion of a key by which said volume-adjustment male member is alternately screwable upwardly and downwardly along said female threaded structure.

8. The transdermal cell of claim 1, in which said bottom closure structure having a transverse axis transverse to said longitudinal axis and includes laterally-extending structure extending along said transverse axis in juxtaposition to closure structure bottom end a distance greater than said first dimension as measured from a center of said upwardly extending bottom closure male member.

9. The transdermal cell of claim 1, in which said volume-adjustment male member has a longitudinal axis and includes groove forming a first annular groove around said longitudinal axis at a location between said upper threads end and said lower threads end, said first annular liquid-sealing member being mounted sealably within said first annular groove.

10. The transdermal cell of claim 1, in which said bottom closure structure includes an upwardly extending bottom closure male member having bottom closure male threads meshable with said female-threaded structure, said bottom closure threads having an upper bottom closure threads end and an opposite bottom closure threads end and said bottom -closure structure including a closure structure top end in juxtaposition to upper bottom closure threads and said bottom closure structure further including a closure structure bottom end in juxtaposition to said opposite bottom closure threads end.

* * * * *